United States Patent
Watanabe et al.

(10) Patent No.: US 9,228,952 B2
(45) Date of Patent: Jan. 5, 2016

(54) HEMATOPOIETIC STEM CELL IDENTIFICATION PROBE

(71) Applicant: CANON KABUSHIKI KAISHA, Tokyo (JP)

(72) Inventors: Kohei Watanabe, Brookline, MA (US); Tsuyoshi Nomoto, Tokyo (JP); Mie Okano, Moriya (JP); Taichi Shintou, Saitama (JP); Takeshi Miyazaki, Ebina (JP); Yasuhiko Tabata, Kyoto (JP); Hiroshi Kohara, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 72 days.

(21) Appl. No.: 13/938,915

(22) Filed: Jul. 10, 2013

(65) Prior Publication Data

US 2014/0017722 A1    Jan. 16, 2014

(30) Foreign Application Priority Data

Jul. 11, 2012    (JP) .................................. 2012-155812

(51) Int. Cl.
   *C12Q 1/04*    (2006.01)
   *G01N 21/64*   (2006.01)
   *G01N 33/50*   (2006.01)
   *G01N 33/52*   (2006.01)

(52) U.S. Cl.
   CPC ........ *G01N 21/6486* (2013.01); *G01N 33/5073* (2013.01); *G01N 33/52* (2013.01)

(58) Field of Classification Search
   CPC   G01N 21/6486; G01N 33/5073; G01N 33/52
   See application file for complete search history.

(56) References Cited

U.S. PATENT DOCUMENTS

| | | |
|---|---|---|
| 7,718,379 B2 | 5/2010 | Nilsson et al. |
| 7,985,288 B2 | 7/2011 | Shintou et al. |
| 2005/0003460 A1 | 1/2005 | Nilsson et al. |
| 2007/0128176 A1* | 6/2007 | Habener et al. ............ 424/93.21 |
| 2011/0020314 A1 | 1/2011 | Nilsson et al. |
| 2011/0182810 A1 | 7/2011 | Nomoto et al. |
| 2011/0189096 A1 | 8/2011 | Watanabe et al. |
| 2011/0236310 A1* | 9/2011 | Watanabe et al. ............ 424/1.69 |
| 2011/0243850 A1 | 10/2011 | Shintou et al. |
| 2012/0207683 A1 | 8/2012 | Tanaka et al. |
| 2013/0280169 A1 | 10/2013 | Watanabe et al. |

FOREIGN PATENT DOCUMENTS

| | | |
|---|---|---|
| EP | 2 489 665 A1 | 8/2012 |
| JP | 2004-242513 A | 9/2004 |
| JP | 2009-232853 A | 10/2009 |
| JP | 2010-095562 A | 4/2010 |
| JP | 2011-6560 A | 1/2011 |
| JP | 2012-084431 A | 4/2012 |
| WO | 2007/010586 A1 | 1/2007 |
| WO | 2010/074326 A1 | 7/2010 |

OTHER PUBLICATIONS

Kohara et al. Biomaterials (Jan. 2013) 34: 1024-1032, available online Nov. 9, 2013.*
Watanabe et al. BMC Neuroscience (2012) 12:101.*
Margaret A. Goodell et al., "Isolation and Functional Properties of Murine Hematopoietic Stem Cells that are Replicating in Vivo," 183 J. Exp. Med. 1797-1806 (Apr. 1996).
Norman S. Wolf et al., "In vivo and in vitro Characterization of Long-Term Repopulating Primitive Hematopoietic Cells Isolated by Sequential Hoechst 33342-Rhodanline 123 FACS Selection," 21 Exp. Hematol. 614-622 (1993).
Non-final Office Action in U.S. Appl. No. 13/133,357 (mailed Jun. 2, 2014).
Non-final Office Action in U.S. Appl. No. 13/133,381 (mailed Jun. 2, 2014).
Ariane Jansma et al., "Automated Microflow NMR: Routine Analysis of Five-Microliter Samples," 77 Anal. Chem. 6509-6515 (Aug. 2005).
Margaret A. Goodell et al., "Stem Cell Identification and Sorting Using the Hoechst 33342 Side Population (SP)," pp. 9-18-1-9-18-11 (May 2001) (XP055080021).
Extended European Search Report in European Application No. 13003430.9 (dated Oct. 4, 2013).

* cited by examiner

*Primary Examiner* — Susan Hanley
(74) *Attorney, Agent, or Firm* — Fitzpatrick, Cella, Harper & Scinto

(57) ABSTRACT

The present invention provides a hematopoietic stem cell identification probe. A hematopoietic stem cell analysis probe containing, as an active ingredient, one or more compounds represented by the general formula (1) has been developed:

General formula (1)

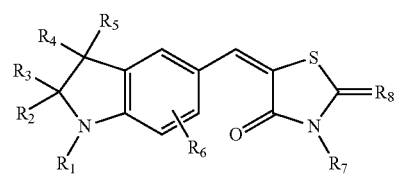

22 Claims, 2 Drawing Sheets

HEMATOPOIETIC STEM CELL IDENTIFICATION PROBE

BACKGROUND OF THE INVENTION

1. Field of the Invention

The present invention relates to a hematopoietic stem cell identification probe, and a method and a kit using a hematopoietic stem cell identification probe.

2. Description of the Related Art

A hematopoietic stem cell is a cell that has multipotency of differentiating into any of all types of blood cells including leucocytes (such as a granulocyte, a lymphocyte, a monocyte and a macrophage), a erythrocyte, a platelet, a mast cell and a denderitic cell, and has replication competence. As a treatment for diseases causing a damage in the hematopoietic function, for example, hematological cancers such as leukaemia, malignant lymphoma and multiple myeloma, or aplastic anemia, transplantation of hematopoietic stem cells accompanied by chemotherapy and radiation therapy has been established.

For performing the transplantation of hematopoietic stem cells, it is necessary to efficiently collect cells including hematopoietic stem cells from umbilical cord blood, bone marrow, peripheral blood or the like and to identify, segregate and enrich the collected cells. Furthermore, use of hematopoietic stem cells of mammals other than a human (such as a mouse and a rat) has been earnestly studied as a model for clarifying mechanism of differentiating and mechanism of maintaining an undifferentiated state of somatic stem cells, and also in such studies, there is a demand for an efficient method for identifying, segregating and enriching hematopoietic stem cells.

As a method for segregating hematopoietic stem cells, a method in which a monocyte component is taken out by using a blood component centrifuge and surfaces of hematopoietic stem cells are labeled with magnetic beads so as to segregate the hematopoietic stem cells from unlabeled cells, or a method using a cell sorter is employed.

If a cell sorter is used, a method of selectively sorting cells labeled with a cell surface marker and a method of sorting cells having a dye excretion property are known, and cells can be highly accurately segregated by such a method.

As for fractions obtained by using a cell sorter with a cell surface marker used, it has been clarified that a fraction having a pattern of a cell surface antigen expression of c-Kit positive, Sca-1 positive and lineage marker negative (a KSL fraction) and, with respect to those obtained from a mouse, a fraction further being CD34 negative or a CD34 negative-KSL fraction and a KSL-SP fraction contain hematopoietic stem cells in a high concentration, and these fractions are frequently used in the same sense as hematopoietic stem cells. C-Kit is known to be expressed in all hematopoietic precursor cells having multipotency similar to that of hematopoietic stem cells and can be used as a simple marker for hematopoietic stem cells and undifferentiated hematopoietic cells including hematopoietic precursor cells. Furthermore, it has been reported that hematopoietic stem cells are enriched in CD150 positive and CD48 negative fractions, and such a fraction is used singly or together with a CD34 negative-KSL fraction.

Furthermore, a method using JAM-1 as a marker (Japanese Patent Application Laid-Open No. 2004-242513), a method using Robo-4 protein as a maker (WO2007/010586) and a method using a marker for hyaluronic acid present on a cell surface (Japanese Patent Application Laid-Open No. 2009-232853) have been disclosed.

On the other hand, as a method using a dye, a method of enriching a SP (side population) of cells specifically excreting Hoechst 33342 bound to DNA is widely known (Goodell M A et al., J Exp Med. 1996; 183, 1797-1806). Moreover, it has been disclosed that Rhodamine 123 is excreted by hematopoietic stem cells (Wolf, N S et al., Exp Hematol. 1993; 21, 614-622).

If a hematopoietic stem cell enriched cell population is easily identified and separated, not only it is extremely useful in transplantation of enriched/separated hematopoietic stem cells for reproducing the hematogenous function of a patient having been given a medical treatment causing a damage in hematopoiesis, such as a chemotherapy for a cancer, but also it makes it possible to perform image analysis of hematopoietic stem cells, to identify a bioactive substance affecting the behavior of hematopoietic stem cells, and the like.

The methods of segregating/enriching hematopoietic stem cells using a cell surface marker disclosed in Japanese Patent Application Laid-Open No. 2004-242513, WO2007/010586, Japanese Patent Application Laid-Open No. 2009-232853 and the like had, however, problems, for example, in which it costs much because a plurality of expensive monoclonal antibodies and the like are used in combination, the functions of segregated cells may be inhibited by an antibody, and a blocking operation for preventing non-specific adsorption of an antibody may be required in some cases.

On the other hand, the method using a dye is superior in a point where a reagent is available inexpensively as compared with an antibody, but it is necessary to excite Hoechst 33342 at a wavelength in the vicinity of 350 nm. Although an ultraviolet laser is necessary for coping with this wavelength, an ultraviolet laser is too expensive to be provided on a general cell sorter apparatus, and therefore, Hoechst 33342 could not be widely used. Moreover, since Hoechst 33342 is a DNA-binding dye, there was a problem in which Hoechst 33342 should be carefully handled because there is a risk of mutagenicity. The Rhodamine 123 disclosed by Wolf, N S et al., in Exp Hematol. 1993; 21, 614-622 is excited at a wavelength in the vicinity of 500 nm and hence the fluorescence can be detected by an inexpensive analyzer. The Rhodamine 123 is, however, excreted by many hematopoietic cells other than hematopoietic stem cells, and hence is less efficiently used for enrichment of hematopoietic stem cells.

SUMMARY OF THE INVENTION

The present inventors have made earnest studies for solving the aforementioned problems, and as a result of the studies, the present inventors have found that incorporation of a compound represented by the following general formula (1) by hematopoietic stem cells is lower than that by other hematopoietic cells, and thus, a hematopoietic stem cell identification probe of the present invention was accomplished.

Specifically, the present inventors provide a hematopoietic stem cell identification probe for identifying hematopoietic stem cells, containing at least one or more compounds selected from the group consisting of compounds represented by general formula (1):

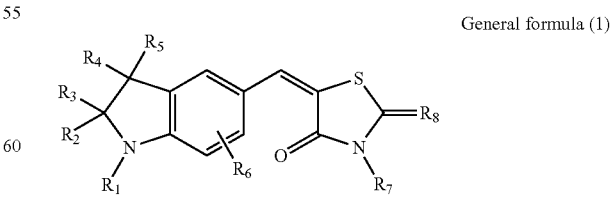

General formula (1)

wherein $R_1$ represents a hydrogen atom, an alkyl group, an aralkyl group, an alkenyl group, an aryl group or a hetero ring group; $R_2$ to $R_5$ each independently represent a hydrogen atom or an alkyl group, with $R_2$ and $R_4$ optionally bound to each other for forming a ring; $R_6$ represents a hydrogen atom, an alkyl group, an alkoxy group or a halogen atom; $R_7$ represents an alkyl group or a carboxyalkyl group; and $R_8$ represents a sulfur atom or a group represented by general formula (4):

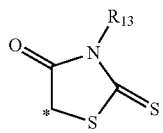

General formula (4)

wherein a sign * represents a bonding site to the compound of the general formula (1); and $R_{13}$ represents an alkyl group or a carboxyalkyl group.

Furthermore, the present inventors have developed and provide an identification method, a separation method, an evaluation method, an analysis method, a screening method and a kit using a hematopoietic stem cell identification probe.

By providing a hematopoietic stem cell identification probe of the present invention, hematopoietic stem cells can be analyzed by a simple, safe and inexpensive method. Furthermore, hematopoietic stem cells can be efficiently segregated/enriched and evaluated, and a bioactive substance affecting hematopoietic stem cells can be evaluated and analyzed.

Further features of the present invention will become apparent from the following description of exemplary embodiments with reference to the attached drawings.

DESCRIPTION OF THE EMBODIMENTS

Figure 1:
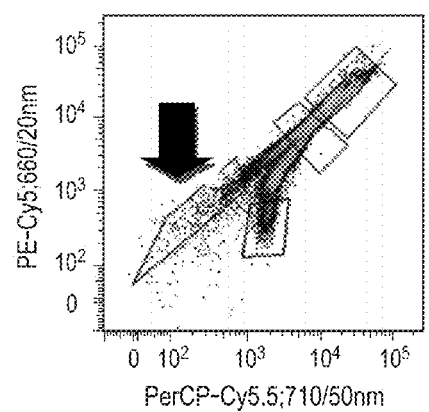
FIG. 1 is a diagram of a cytogram of bone marrow cells exposed to a stain in Experimental Example 1 developed with respect to two kinds of fluorescent signals derived from a compound 7.

Preferred embodiments of the present invention will now be described in detail in accordance with the accompanying drawings.

(Hematopoietic Stem Cell Identification Probe)

The present invention provides a hematopoietic stem cell identification probe as a first embodiment.

A hematopoietic stem cell identification probe of the present invention is a hematopoietic stem cell identification probe for identifying hematopoietic stem cells by utilizing lower incorporation by hematopoietic stem cells than by the other cells, and contains at least one or more compounds selected from the group consisting of compounds represented by the general formula (1):

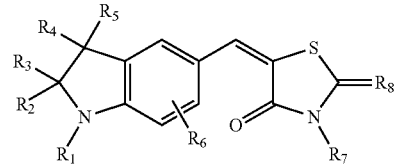

General formula (1)

wherein $R_1$ represents a hydrogen atom, an alkyl group, an aralkyl group, an alkenyl group, an aryl group or a hetero ring group; $R_2$ to $R_5$ each independently represent a hydrogen atom or an alkyl group, with $R_2$ and $R_4$ optionally bound to each other for forming a ring; $R_6$ represents a hydrogen atom, an alkyl group, an alkoxy group or a halogen atom; $R_7$ represents an alkyl group or a carboxyalkyl group; and $R_8$ represents a sulfur atom or a group represented by the general formula (4):

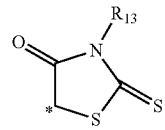

General formula (4)

wherein a sign * represents a binding site to the general formula (1); and $R_{13}$ represents an alkyl group or a carboxyalkyl group.

The alkyl group of $R_1$ in the above general formula (1) is not limited, and examples include a methyl group, an ethyl group, a propyl group and a butyl group.

The aralkyl group of $R_1$ is not limited, and examples include a benzyl group and a phenethyl group.

The alkenyl group of $R_1$ is not limited, and an example includes an alkenyl group having 2 to 20 carbon atoms such as a vinyl group, a 2,2-diphenylvinyl group, a 3-butenyl group or a cyclohexenyl group.

The aryl group of $R_1$ is not limited, and examples include a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

The hetero ring group of $R_1$ is not limited, and examples include a pyridyl group, a pyrazyl group, a pyrimidyl group, a thienyl group, a furyl group, a morpholinyl group and a piperidinyl group.

The substituent $R_1$ can be independently and arbitrarily selected from the aforementioned substituents, and in an exemplary embodiment, an aralkyl group, an alkenyl group, an aryl group or the like can be used because of high fluorescence intensity, and more specifically, a phenyl group, a 4-bromophenyl group, a 4-methoxyphenyl group, a 3-thiomethylphenyl group, a 4-thiomethylphenyl group or the like is particularly preferably used.

The alkyl group of $R_2$ to $R_5$ in the above general formula (1) is not limited, and examples include a methyl group, an ethyl group, a propyl group, a butyl group, a pentyl group and a hexyl group.

The aryl group of $R_2$ to $R_5$ is not limited, and examples include a phenyl group and a naphthyl group.

The ring formed by $R_2$ and $R_4$ bound to each other is not limited, and examples include a saturated aliphatic ring such as a cyclooctane ring, a cycloheptane ring, a cyclohexane ring, a cyclopentane ring or a cyclobutane ring, and a partially saturated aliphatic ring such as a cyclopentene ring or a cyclohexene ring.

As for the substituents $R_2$ to $R_5$, a case where the substituents independently represent a hydrogen atom, an alkyl group or an aryl group and the substituents $R_2$ and $R_4$ are bound to each other for forming a ring is preferred, and a case where the substituents $R_2$ and $R_4$ are bound to each other for forming a ring is more preferred because the chemical structure is stable in such a case. Specific examples of the ring include a cyclooctane ring, a cycloheptane ring, a cyclohexane ring, a cyclopentane ring and a cyclobutane ring. A cyclopentane ring is more preferable for an analysis probe because of particularly low fluorescence intensity attained when exposed to hematopoietic stem cells.

The alkyl group of $R_6$ in the above general formula (1) is not limited, and examples include a methyl group, an ethyl group, a propyl group and a butyl group.

The alkoxy group of $R_6$ in the above general formula (1) is not limited, and examples include a methoxy group, an ethoxy group, a propoxy group and a butoxy group.

Examples of the halogen atom of $R_6$ include a fluorine atom, a chlorine atom, a bromine atom and an iodine atom.

The substituent $R_6$ represents preferably a hydrogen atom, a halogen atom or an alkoxy group, and more preferably a hydrogen atom or a halogen atom. Among halogen atoms, a bromine atom is preferred.

The alkyl group of $R_7$ is not limited, and examples include a methyl group, an ethyl group, a propyl group, a butyl group, a pentyl group, a hexyl group, a heptyl group and an octyl group.

The carboxyalkyl group of $R_7$ (in which —$CH_2$—$CH_2$— in a carbon chain may be substituted with —CONH—) is not limited, and examples include an acetic acid group, a propionic acid group, a butanoic acid group and the following compounds 1 to 6. In each of these compounds, a sign * represents a binding site to N.

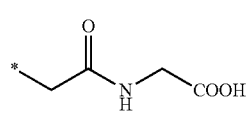

(1)

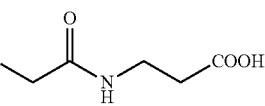

(2)

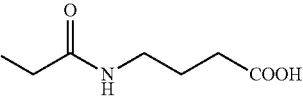

(3)

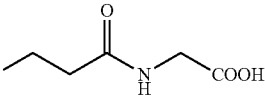

(4)

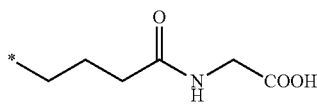

(5)

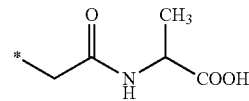

(6)

The substituent $R_{13}$ in the general formula (4) is not limited, and examples include an alkyl group such as a methyl group, an ethyl group, a propyl group, a butyl group, a pentyl group, a hexyl group, a heptyl group or an octyl group; and an aralkyl group such as an allyl group, a carboxyalkyl group or a benzyl group.

A hematopoietic stem cell refers to, as described above, a cell that has multipotency of differentiating into any of all types of blood cells including leucocytes (such as a granulocyte, a lymphocyte, a monocyte and a macrophage), a erythrocyte, a platelet, a mast cell and a denderitic cell, and has replication competence. Incidentally, cells contained in a fraction identified as hematopoietic stem cells based on a pattern of a cell surface antigen expression may be sometimes used in the same sense. Examples of the fraction identified as hematopoietic stem cells include a fraction having a pattern of a cell surface antigen expression of c-Kit positive, Sca-1 positive and lineage marker negative (a KSL fraction) and, with respect to those obtained from a mouse, a KSL fraction further being CD34 negative or a CD34 negative-KSL fraction, a KSL-SP fraction, a CD150 positive CD48 negative fraction, and a fraction of an SP enriched with cells having a high excretive property for Hoechst 33342.

The hematopoietic stem cells of the present invention may include hematopoietic precursor cells having multipotency similar to that of the hematopoietic stem cells. As a marker for the hematopoietic stem cells and the hematopoietic precursor cells, c-Kit may be used as a simple marker. As one of functional evaluation methods for the hematopoietic stem cells and the hematopoietic precursor cells, a hematopoietic colony forming assay is performed for evaluating hematopoietic colony forming ability.

The other cells herein refer to cells other than the hematopoietic stem cells. In consideration that the hematopoietic stem cell identification probe of the present invention is frequently used for identifying the hematopoietic stem cells included in cells contained particularly in a bone marrow aspirate, or blood such as peripheral blood or umbilical cord blood, examples of the other cells include already differentiated cells included in a bone marrow aspirate or blood, and more specifically, the examples include matured leucocytes (such as granulocytes, lymphocytes, monocytes and macrophages), erythrocyte, platelet, mast cell and denderitic cell.

Herein, incorporation by a cell refers to that a cell incorporates a substance somehow, and specifically that a substance is incorporated into, for example, a cell membrane, a cytoplasm, a nucleus, a cell organelle or the like. A mechanism of the incorporation is not questioned, and examples of the mechanism include endocytosis, covalent bond, and incorporation into a cell membrane by a hydrophobic effect. Incidentally, high incorporation means that a substance is highly efficiently incorporated, and low incorporation means that a substance is lowly efficiently incorporated. It can be determined whether incorporation is high or low based on properties of an incorporated substance. For example, the determination can be appropriately made based on absorbance if the substance is a dye, based on a degree of light emission attained by irradiation with excitation light if the substance has a fluorescent characteristic, and based on a property such as electrochemical activity, or magnetic activity if the substance has such a property.

When incorporated by a cell, the compound of the present invention is changed in fluorescence intensity thereof. Specifically, when the compound is incorporated by a cell, the fluorescence intensity is enhanced by twice or more, more preferably five times or more as compared with that attained before the incorporation.

Owing to the characteristic that the fluorescence is enhanced when incorporated by a cell, the fluorescence intensity is increased when the hematopoietic stem cell identification probe of the present invention is incorporated by a cell other than a hematopoietic stem cell, which increases a difference in the fluorescence intensity from a hematopoietic stem cell not incorporating the probe, so that the hematopoietic stem cell can be clearly distinguished. Furthermore, since background is relatively lowered, the cell having incorporated the probe can be identified without performing a washing operation after staining.

It is regarded that the enhancement of the fluorescence intensity is brought through the following mechanisms: 1) Dispersibility of fluorescent molecules is improved when incorporated by a cell, and hence, a concentration quenching effect is lowered, resulting in increasing the fluorescence intensity; and 2) fluorescent molecules become rigid by adsorbing onto biomolecules, so as to increase fluorescence quantum yield.

Incidentally, cells mentioned herein are not limited in biological species, and examples include, as vertebrates, teleosts such as a tiger puffer, a grass puffer, a green spotted puffer, a cyprinodont and a zebra fish, amphibians such as a *Xenopus laevis*, birds such as a chicken and a quail, small animals such as a rat, a mouse and a hamster, large animals such as a goat, a pig, a dog, a cat, a cattle or a horse, and primates such as a monkey, a chimpanzee and a human. Before collecting cells, G-CSF may be administered to an individual for increasing hematopoietic stem cells.

The concentration of the compound contained in the hematopoietic stem cell identification probe of the present invention is not limited and may be appropriately adjusted, and the compound is used generally in a concentration of 0.001 ng/mL or more and 100 μg/mL or less and more preferably in a concentration of 0.01 ng/mL or more and 10 μg/mL or less.

The hematopoietic stem cell identification probe of the present invention uses at least one or more compounds represented by the above general formula (1) dissolved in an appropriate solvent. The solvent is not limited, and can be one less affecting cells or an organism, and for example, an aqueous liquid having high affinity with an organism can be used. Specific examples include water; saline; phosphate buffered saline (PBS); a buffer such as Tris buffer; a cell culture medium such as D-MEM (Dulbecco's Modified Eagle Medium) or HBSS (Hanks' Balanced Salt Solutions), a commercially available buffer for FACS analysis, and an infusion solution such as a lactated Ringer solution. Such a solvent can particularly contain 50% or more of water. Besides, a mixture of two or more of these solvents may be used. Furthermore, a serum such as a fetal bovine serum (FBS) or a horse serum, or an antibacterial agent such as sodium azide may be added to such a solvent before use. In particular, saline; phosphate buffered saline (PBS); a buffer such as Tris buffer; a cell culture medium such as D-MEM (Dulbecco's Modified Eagle Medium) or HBSS (Hanks' Balanced Salt Solutions), a commercially available buffer for FACS analysis, an infusion solution such as a lactated Ringer solution or the like can be used from the viewpoint of controlling a salt concentration, pH and the like suitably for cells.

Besides, one additive or more additives in combination may be added if necessary. The additives used in the present invention are not limited as long as the hematopoietic stem cell identification probe is not affected, and examples include a humectant, a surface tension regulator, a thickener, salts such as sodium chloride, various pH adjustors, a pH buffer, an antiseptic agent, an anti-fungus agent, a sweetener and a perfume.

A method for preparing the hematopoietic stem cell identification probe of the present invention is not limited, and the hematopoietic stem cell identification probe may be prepared by, for example, diluting a concentrated solution of the compound dissolved in any of the aforementioned solvents. If the water-solubility of the compound is low, the compound may be dissolved in an appropriate solvent before dilution. For producing a concentrated solution, an alcohol solvent such as methanol, ethanol, isopropanol, butanol, ethylene glycol or glycerin; or an organic solvent such as N,N-dimethyl sulfoxide (hereinafter abbreviated as "DMSO") or N,N-dimethyl formamide (hereinafter abbreviated as "DMF") can be used. Among these solvents, methanol, ethanol or DMSO is particularly preferred.

The compound contained in the hematopoietic stem cell identification probe of the present invention has a characteristic that the compound works as a substrate of at least one or more drug transporters. The drug transporter is not limited, and examples include an ABC transporter, an SLC transporter, a glucose transporter and a dopamine transporter. Among these drug transporters, an efflux transporter is preferred, an ABC transporter is more preferred, and a transporter working as a substrate of Pgp, BCRP (breast cancer resistance protein) or MRP (multidrug resistance-associated protein) is still more preferred.

To "work as a substrate of a drug transporter" means that the compound can be selectively transported by an influx transporter or that the compound cannot be transported or migration of the compound via the drug transporter is changed in the presence of an influx transporter inhibitor. Alternatively, it means that the compound is selectively transported by an efflux transporter, that the compound can be transported by the drug transporter in the absence of an efflux transporter inhibitor but cannot be transported in the presence of the inhibitor, or that migration of the compound via the drug transporter is changed in the presence of an efflux transporter inhibitor.

The compounds represented by the general formula (1) of the present invention can be synthesized by a known method (such as one described in Japanese Patent Application Laid-Open No. 2010-095562).

The hematopoietic stem cell identification probe of the present invention can more preferably contain, as an active ingredient, at least one of compounds represented by the following general formula (2):

General formula (2)

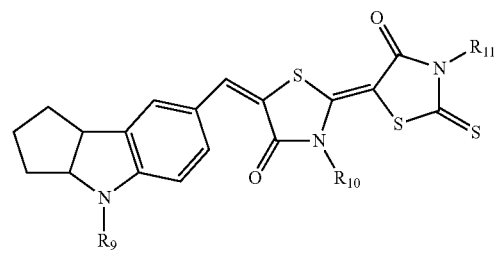

wherein $R_9$ represents an aryl group; $R_{10}$ represents an alkyl group or a carboxyalkyl group, and $R_{11}$ represents an alkyl group, an aralkyl group, an allyl group or a carboxyalkyl group.

The aryl group of $R_9$ in the above general formula (2) is not limited, and examples include a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

Furthermore, for an analysis probe, $R_9$ preferably represents a phenyl group, a 4-bromophenyl group, a 4-methoxyphenyl group, a 3-thiomethylphenyl group, a 4-thiomethylphenyl group or the like because such a group shows low fluorescence intensity when exposed to hematopoietic stem cells. Particularly, a 4-methoxyphenyl group is superior.

The alkyl group of $R_{10}$ and $R_{11}$ in the above general formula (2) is not limited, and examples include a methyl group, an ethyl group, a propyl group, a butyl group, a pentyl group and a hexyl group.

The carboxyalkyl group of $R_{10}$ is not limited, and examples include a carboxymethyl group, a carboxypropyl group and a carboxybutyl group.

The aralkyl group of $R_{11}$ is not limited, and examples include a benzyl group and a phenethyl group.

The carboxyalkyl group of $R_{11}$ is not limited, and examples include a carboxymethyl group, a carboxypropyl group and a carboxybutyl group.

Furthermore, the hematopoietic stem cell identification probe of the present invention can contain, as an active ingredient, at least one of compounds represented by the following general formula (3):

General formula (3)

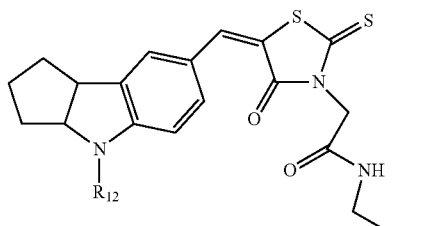

wherein $R_{12}$ represents an aryl group.

The aryl group of $R_{12}$ in the above general formula (3) is not limited, and examples include a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

More specifically, for an analysis probe, a phenyl group, a 4-bromophenyl group, a 4-methoxyphenyl group, a 3-thiomethylphenyl group, a 4-thiomethylphenyl group or the like is preferred because such a group particularly shows low fluorescence intensity when exposed to hematopoietic stem cells. In particular, a 4-methoxyphenyl group is superior.

Preferable specific examples of the compounds represented by the general formula (1) of the present invention include the following compounds 7 to 23. These compounds emit light in response to excitation light of a wavelength of 400 to 700 nm and more preferably in response to excitation light of a wavelength of 450 to 650 nm. As for a compound that emits light in response to excitation light of a wavelength in the vicinity of 455 to 530 nm, a highly versatile inexpensive analyzer equipped with a 488 nm laser can be used.

(7)

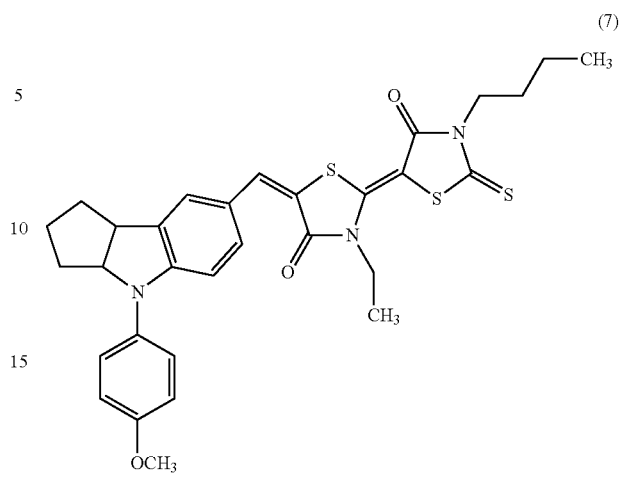

(8)

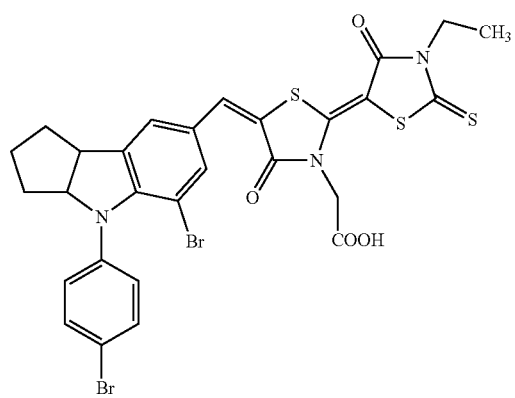

(9)

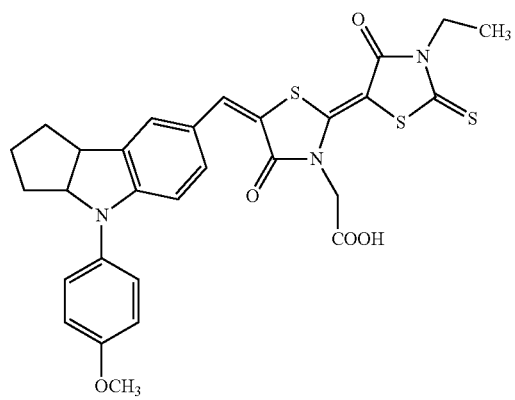

(10)

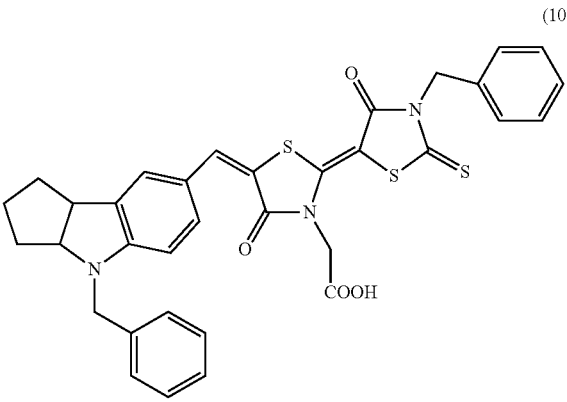

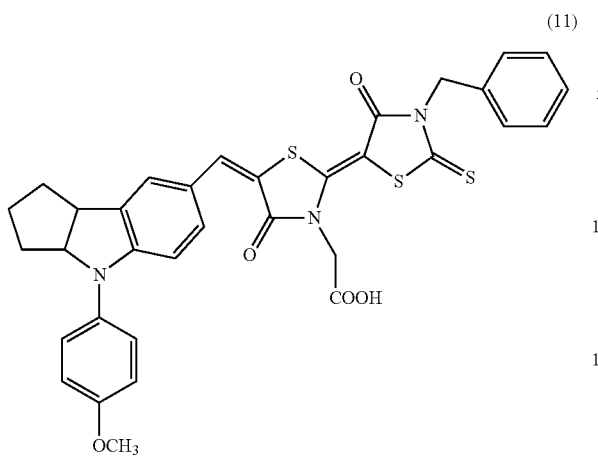
(11)
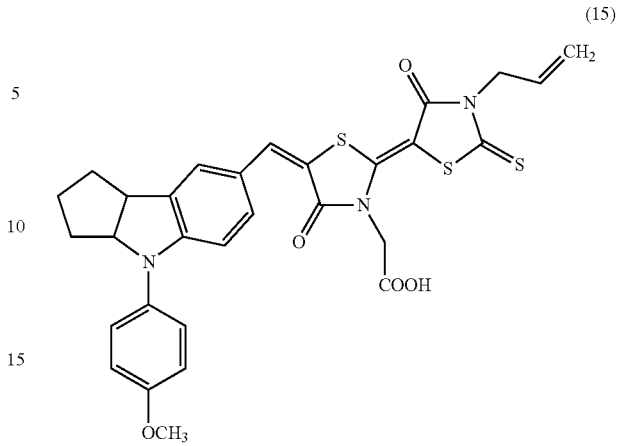
(15)
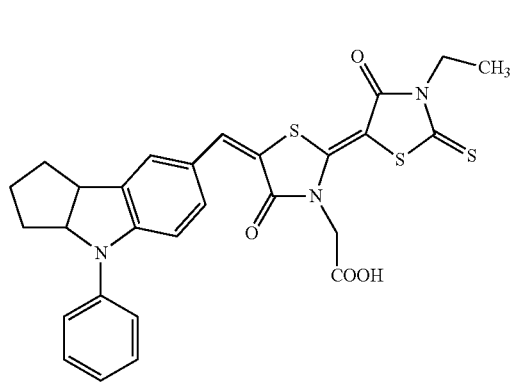
(12)
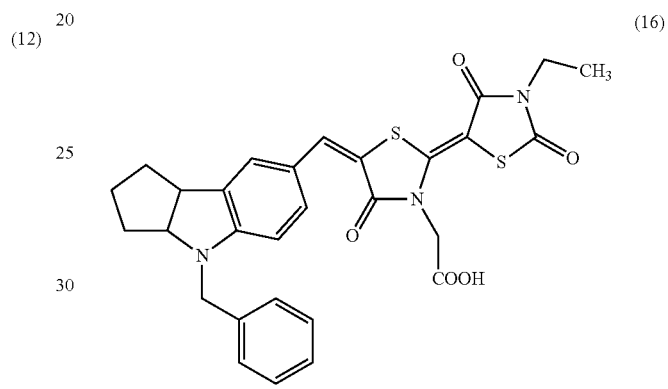
(16)
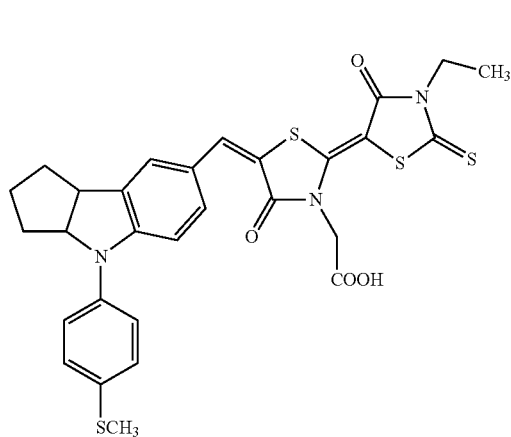
(13)
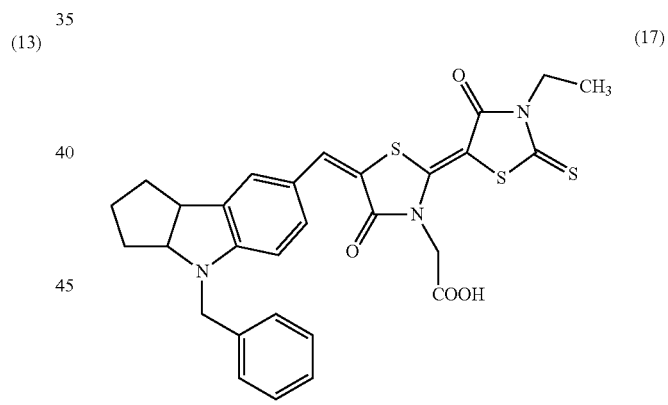
(17)
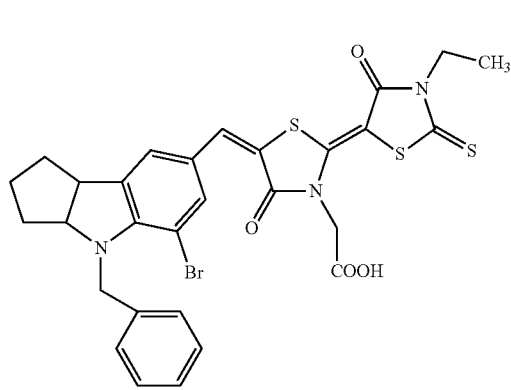
(14)
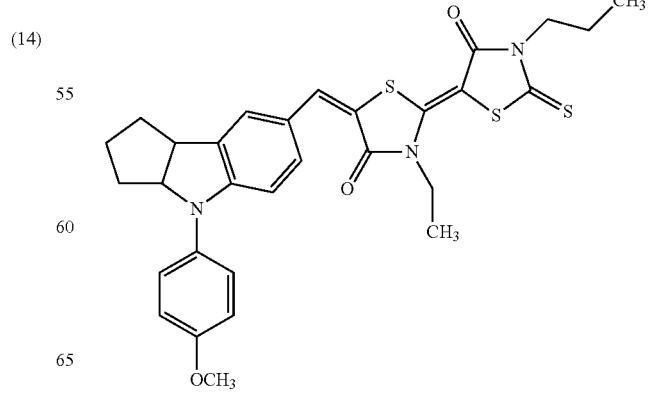
(18)

(19)
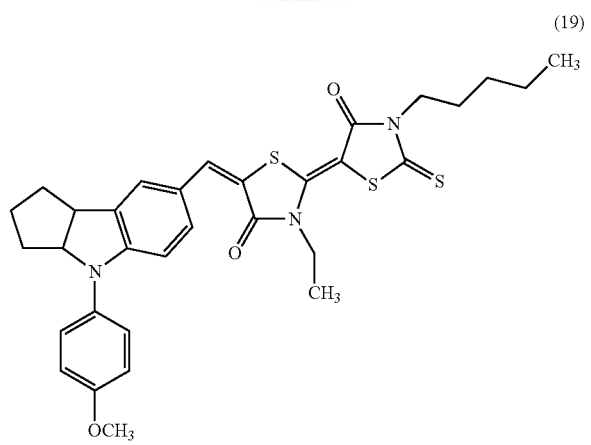
(20)
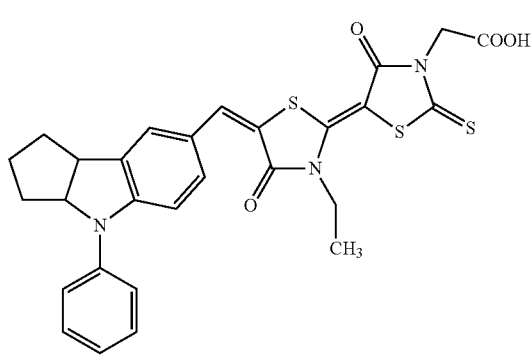
(21)
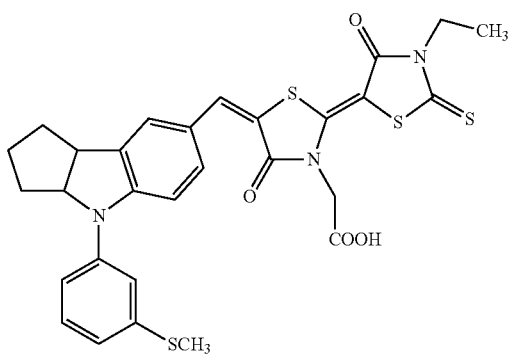
(22)
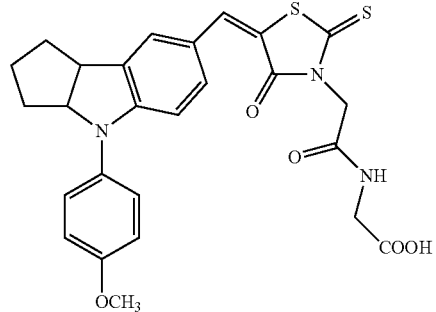
(23)
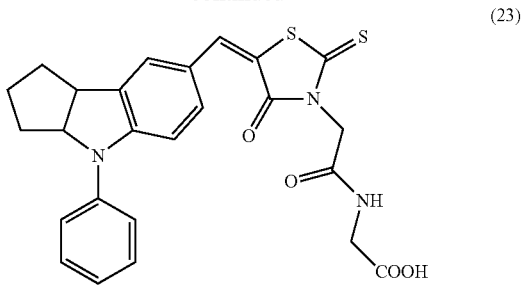
Incidentally, among the aforementioned compounds, the following compounds 7, 18, 19, 22 and 23 are particularly preferred.
(7)
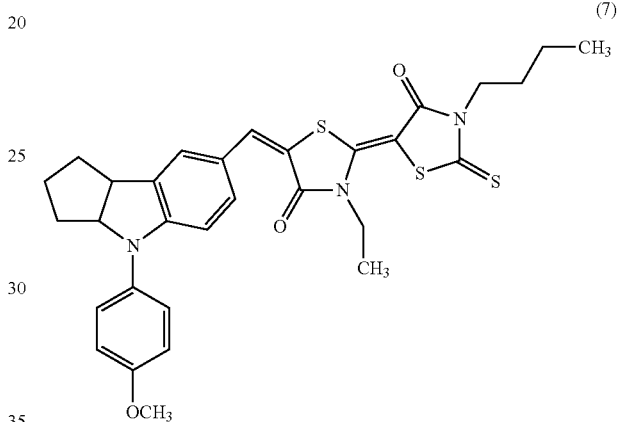
(18)
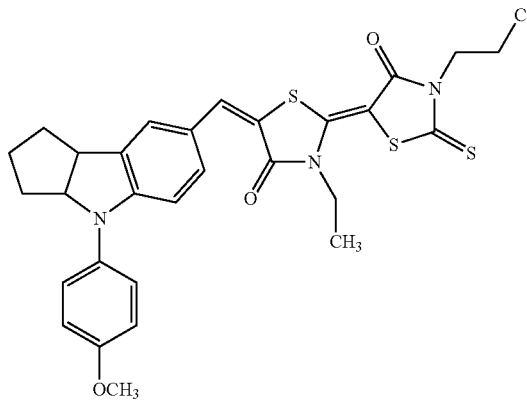
(19)
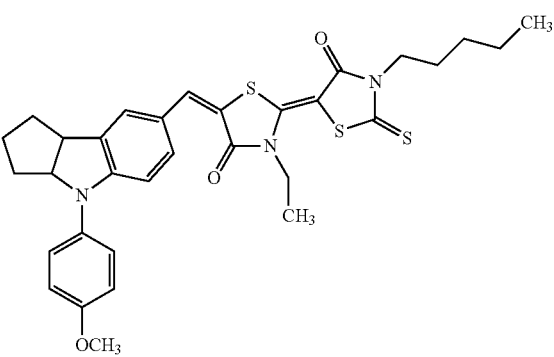

-continued

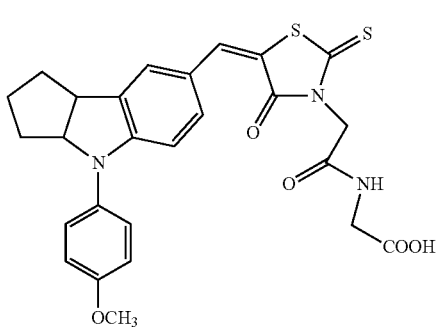

(22)

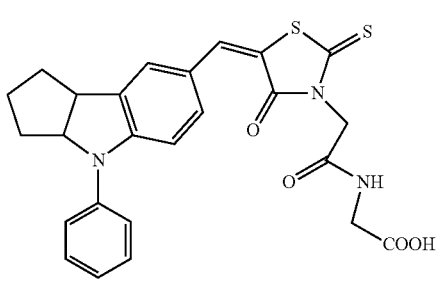

(23)

(Identification Method for Hematopoietic Stem Cells)

The present invention provides an identification method for hematopoietic stem cells as a second embodiment. Specifically, the present invention provides an identification method in which the hematopoietic stem cell identification probe of the present invention is provided to a cell population and hematopoietic stem cells contained in the cell population are identified based on incorporation of the hematopoietic stem cell identification probe.

Furthermore, a cell with low incorporation of the hematopoietic stem cell identification probe can be identified as a hematopoietic stem cell, and if the hematopoietic stem cell identification probe has a fluorescent characteristic, a hematopoietic stem cell contained in a cell population can be identified based on the fluorescence.

The identification method for hematopoietic stem cells of the second embodiment of the present invention can be performed, after exposing the hematopoietic stem cell identification probe of the present invention to a cell sample for staining, based on comparison in fluorescence intensity according to amounts of the hematopoietic stem cell identification probe incorporated by cells by flow cytometry or using an identification apparatus for FACS analysis or the like. Alternatively, the identification method can be performed by observing stained cells with a fluorescence microscope and identifying amounts incorporated by the cells based on an image.

<Apparatus>

If the identification is performed by employing the flow cytometry or the identification apparatus for FACS analysis or the like, optical characteristics such as front scatter and side scatter can be simultaneously used, so as to exclude signals or the like derived from particles other than the cells from signals detected by the identification apparatus. Furthermore, dead cells can be stained with a dead cell detection reagent for performing the identification on living cells alone. As the dead cell detection reagent, a commercially available reagent can be suitably used.

<Staining>

The exposure of the hematopoietic stem cell identification probe of the present invention can be performed by mixing, in an appropriate vessel, a cell sample with a stain containing the hematopoietic stem cell identification probe. The temperature at the time of the exposure is not limited, and the exposure can be performed at a temperature of 4 to 42° C., more preferably 4 to 38° C., still more preferably 31 to 38° C., and most preferably 37° C.

The time for the exposure is not limited, and the exposure can be performed for 5 minutes or more and 24 hours or less, more preferably 5 minutes or more and 4 hours or less, and still more preferably 5 minutes or more and 1 hour or less.

<Washing>

After the exposure, a washing operation may be performed as occasion demands. The washing operation can be performed by adding a solution (a washing solution) not containing the hematopoietic stem cell identification probe after removing the stain with the cell sample precipitated by centrifuge. The washing operation may be repeated once or more times as occasion demands. Furthermore, the cell sample may be allowed to remain in the washing solution for a prescribed period of time. The exposed cell sample may be stirred or filtered so as to avoid cell agglutination.

<Identification>

The exposed cell sample is subjected to detection for the optical characteristics such as the fluorescence intensity, the front scatter and the side scatter of each cell contained in the cell sample by the flow cytometry or the identification apparatus for FACS analysis or the like, and the thus obtained data is expanded by dedicated analysis software based on parameters of the optical characteristics for the identification. Alternatively, the identification can be performed based on a difference in the incorporation by observing the exposed cell sample with a fluorescence microscope. When the hematopoietic stem cell identification probe of the present invention is used, a hematopoietic stem cell can be identified as a cell with low intensity of fluorescence derived from the hematopoietic stem cell identification probe. The fluorescence derived from the hematopoietic stem cell identification probe can be detected with a combination of a plurality of excitation light and fluorescence wavelengths by irradiation with a plurality of excitation light and detection of a plurality of fluorescence. If a plurality of excitation light and fluorescence wavelengths are combined, the fluorescence wavelength of the incorporated hematopoietic stem cell identification probe changed according to the kind of cells can be detected, and hence, the thus obtained information is useful for identifying the kind of cells.

In the case where the observation with a microscope is employed, a light emitting portion and a non-light emitting portion can be easily detected by imaging the cell population with the hematopoietic stem cell identification probe allowed to emit light within a cell by irradiating the cell with excitation light. Alternatively, a bright field image obtained under irradiation with visible light and a fluorescence image obtained under irradiation with excitation light can be combined by an image processing unit, so as to observe a distribution of hematopoietic stem cells in the cell in more details. Besides, a confocal microscope can be used because an optical slice image can be thus obtained. Furthermore, a multiphoton excitation fluorescence microscope is suitably used for observation of the inside of a cell population because the multiphoton excitation fluorescence microscope has high deep reachability and high spatial resolution.

(Separation Method for Hematopoietic Stem Cells)

The present invention provides a separation method for hematopoietic stem cells as a third embodiment. Specifically, the present invention provides a separation method for separating hematopoietic stem cells by employing the identification method for hematopoietic stem cells of the second embodiment.

More specifically, the separation method can be performed by providing the hematopoietic stem cell identification probe of the present invention and selectively collecting (sorting)

hematopoietic stem cells based on incorporation of the hematopoietic stem cell identification probe. For sorting the cells, a commercially available FACS apparatus is suitably used. If the identification is performed based on an image, the separation method can be performed also by selectively collecting or removing hematopoietic stem cells or cells other than hematopoietic stem cells. For selectively collecting or removing cells, an aspirator or the like can be used. Incidentally, the separation refers to selective segregation or enrichment of hematopoietic stem cells.

(Evaluation Method for Cell Population)

The present invention provides an evaluation method for a cell population as a fourth embodiment.

The evaluation method for a cell population includes a step of exposing the hematopoietic stem cell identification probe of the present invention to a cell sample. Besides, in the evaluation method of the present invention, after or simultaneously with the exposure of the hematopoietic stem cell identification probe to the cell sample, a test substance can be allowed to act on a part or the whole of the cell population. The evaluation method of the present invention further includes a step of detecting incorporation of the hematopoietic stem cell identification probe by cells. Thus, the number or the ratio of hematopoietic stem cells contained in the cell population can be evaluated. If the test substance has been allowed to act, an effect of the test substance on the number or the ratio of hematopoietic stem cells can be evaluated. At this point, if a cell sample affected by the test substance and a cell sample not affected by the test substance are separately evaluated, information on the action of the test substance can be obtained based on change in the number or the ratio of hematopoietic stem cells according to the presence/absence of the test substance. If two or more test substances are used, information on a difference in the action between these test substances can be obtained.

(Analysis Method)

The present invention provides, as a fifth embodiment, an analysis method in which a hematopoietic stem cell identification probe is provided to cells simultaneously with, or before or after providing a substance to the cells and analysis is performed based on incorporation of the hematopoietic stem cell identification probe. The substance may be one affecting identification by the hematopoietic stem cell identification probe or one not affecting the identification. If the substance does not affect the identification by the hematopoietic stem cell identification probe, an interaction of a test substance on hematopoietic stem cells identified by the hematopoietic stem cell identification probe can be detected. For detecting the interaction, fluorescence may be used. If the test substance has fluorescence, in order to perform accurate evaluation, the test substance or a hematopoietic stem cell identification probe can be selected so as to have a different excitation wavelength or a different fluorescence wavelength from the hematopoietic stem cell marker of the present invention. If the excitation wavelengths or the fluorescence wavelengths are different, bond, incorporation or the like of the test substance to or by a hematopoietic stem cell can be analyzed by respectively detecting a fluorescence signal derived from the hematopoietic stem cell marker and a fluorescence signal derived from the test substance. The test substance having fluorescence is not limited but may be a fluorescent surface antibody marker, and examples include organic molecules or inorganic molecules having fluorescence.

(Screening Method)

The present invention provides, as a sixth embodiment, a screening method in which a hematopoietic stem cell identification probe is provided to cells simultaneously with, or before or after providing a substance to the cells and screening is performed on the substance based on incorporation of the hematopoietic stem cell identification probe. In the screening, the aforementioned evaluation method or analysis method of the present invention can be employed for evaluating/analyzing effects of a plurality of test substances on hematopoietic stem cells. For example, a bioactive substance affecting the action of an influx/efflux transporter of a compound expressed in a hematopoietic stem cell can be evaluated. Particularly, the action of an efflux transporter can be suitably evaluated. More preferably, an ABC transporter can be evaluated. In the case where the hematopoietic stem cell identification probe of the present invention is used, if the action of an efflux transporter is inhibited due to the influence of a bioactive substance so that hematopoietic stem cells can be poorly segregated or less different from the other cells, it can be evaluated that the bioactive substance has an action on the efflux transporter.

Alternatively, in order to examine a surface antigen expressed in a hematopoietic stem cell, if a fluorescence-labeled surface antigen antibody is used as a test substance, the kind of antibody having a high bonding property to a hematopoietic stem cell can be screened.

Furthermore, if a fluorescent substance whose incorporation by a hematopoietic stem cell is unknown is used as a test substance, an action of the test substance on the hematopoietic stem cell identified by the hematopoietic stem cell identification probe can be evaluated based on fluorescence intensity.

(Kit)

The present invention provides a kit including a hematopoietic stem cell identification probe as a seventh embodiment. Components of the kit are not limited, and the kit may include a vessel, a reagent and the like necessary for exposing the hematopoietic stem cell identification probe to cells.

Now, examples will be described.

EXAMPLES

Synthesis Example 1

As an example of the probe of the present invention, a synthesis example for the compound 7 will be described.

To a solution of 3.3 g (11.4 mmol) of aldehyde (A) in 20 mL acetic acid, 3.6 g (11.5 mmol) of a compound (B) and 0.9 g of ammonium acetate were added, and the resulting solution was stirred for 2 hours under reflux. After completing the reaction, 50 mL of water was slowly added dropwise thereto with cooling, so as to cool the solution to room temperature. The thus precipitated solid was filtered, washed twice with 100 mL of water and further washed with 50 mL of 2-propanol, so as to obtain 4.0 g (yield 59.9%) of the compound 7. The aldehyde (A) and the compound had the following structures:

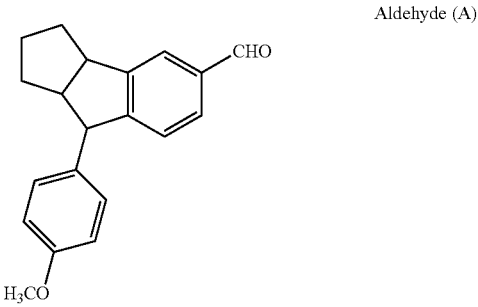

Aldehyde (A)

-continued

Compound (B)

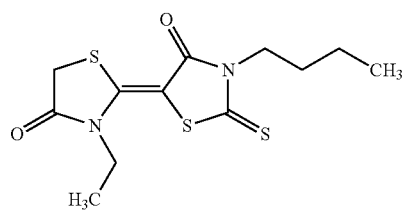

The obtained compound was confirmed to be an aimed substance by 1H nuclear magnetic resonance spectrometry (ECA-400, manufactured by JEOL Ltd.) and LC/TOF MS (LC/MSD TOF, manufactured by Agilent Technologies).

Synthesis Examples for Other Dye Compounds

Other compounds listed in Table 1 below were synthesized by methods similar to that described in Synthesis Example 1 above. The structures of these compounds were confirmed by using the aforementioned analysis apparatuses.

Measurement of Fluorescence Characteristics of Compounds

With respect to each of the compounds 7 to 23, a 5 µM DMSO solution was prepared, and an excitation wavelength and a fluorescence wavelength were measured by using a fluorescence spectrophotometer FL4500 manufactured by Hitachi High-Technologies Corporation (Table 1).

TABLE 1

| Compound | Excitation wavelength $\lambda$ex | Fluorescence wavelength $\lambda$em |
|---|---|---|
| Compound 7 | 539 | 638 |
| Compound 8 | 513 | 600 |
| Compound 9 | 543 | 638 |
| Compound 10 | 540 | 614 |
| Compound 11 | 542 | 643 |
| Compound 12 | 531 | 615 |
| Compound 13 | 539 | 636 |
| Compound 14 | 596 | 520 |
| Compound 15 | 504 | 606 |
| Compound 16 | 500 | 578 |
| Compound 17 | 535 | 612 |
| Compound 18 | 539 | 636 |
| Compound 19 | 538 | 638 |
| Compound 20 | 533 | 615 |
| Compound 21 | 530 | 612 |
| Compound 22 | 511 | 626 |
| Compound 23 | 499 | 598 |

[Evaluation of Hematopoietic Stem Cells by Using hematopoietic Stem Cell Identification Probe]

Experimental Example 1

A 1 mM DMSO solution of the compound 7 was added to an HBSS buffer containing 2% of FBS and 10 mM of HEPES, so as to obtain a stain of the compound 7 in a concentration of 1 µM. Bone marrow cells collected from a femur of a C57BL/6 mouse (of 12 weeks old) and hemolyzed were added to the stain in an amount of $1 \times 10^6$ cells/mL for exposure at 37° C. for 30 minutes. After the exposure, the cells were precipitated by centrifuge for removing the stain, and a blocking treatment was performed with 2.4G2 (anti-mouse Fcγ receptor II/III antibody-producing hybridoma supernatant). The blocked cells were further subjected to immunofluorescence staining with an anti c-Kit antibody, an anti Sca-1 antibody, an anti CD34 antibody and Lineage Marker. Furthermore, the cells were subjected to dead cell staining with TO-PRO-3. The respective antibodies used for fluorescence staining were selected so that the respective fluorescence wavelengths might not overlap one another and might not overlap the fluorescence wavelength of the compound 7 and the fluorescence wavelength of TO-PRO-3. Next, the resulting cells were analyzed with FACS Aria II cell sorter manufactured by BD Biosciences. In the analysis, cell populations having a low TO-PRO-3 signal were regarded as a target, so that the analysis could be performed on a cell population excluding dead cells.

First, fluorescence intensities of the cells obtained by analyzing fluorescence signals derived from the compound 7 based on signal intensities in two channels excited at 488 nm (PE-Cy5; 660/20 nm and PerCP-Cy 5.5; 710/50 nm: center wavelength/wavelength width) were developed into a cytogram. As a result, the bone marrow cells exposed to the stain containing the compound 7 were found to include cells having a wide range of fluorescence intensity as illustrated in FIG. 1.

Figure 2:
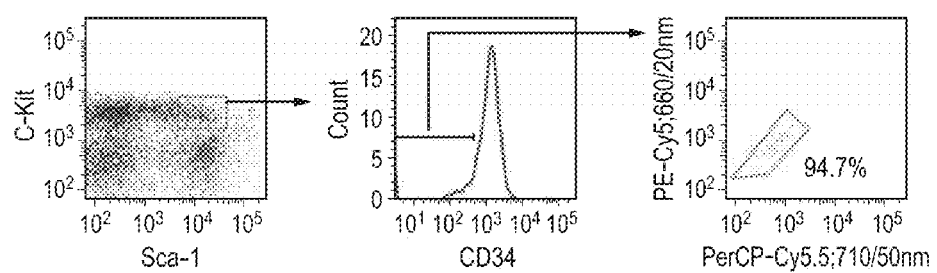
FIG. 2 is a diagram of cytograms of the bone marrow cells of Experimental Example 1 developed based on fluorescent antibody markers and a cytogram of a hematopoietic stem cell fraction obtained by using the fluorescent antibody markers developed with respect to the two kinds of the fluorescent signals derived from the compound 7.

Furthermore, among Lineage Marker negative cell fractions, cell fractions of Sca-1 positive, c-Kit positive and CD34 negative, which are used as markers for hematopoietic stem cells, were developed into cytograms as illustrated in FIG. 2 with respect to the two fluorescence signals derived from the compound 7 as in FIG. 1. As a result, it was found that 94.7% of Lineage Marker negative, Sca-1 positive, c-Kit positive and CD34 negative hematopoietic stem cell fractions had been enriched with a cell population having low incorporation of the probe with respect to both the two fluorescence signals illustrated with an arrow in FIG. 1, and thus, it was confirmed that hematopoietic stem cells can be identified by using the compound 7. Furthermore, merely cells identified by the compound 7 were separated by sorting.

Experimental Examples 2 to 17

Fluorescence signals derived from the compounds 8 to 23 were analyzed in the same manner as in Experimental Example 1 except that the compound 7 used in Experimental Example 1 was changed to each of the compounds 8 to 23. As a result, it was found that hematopoietic stem cells can be identified also by using the compounds 8 to 23 as shown in Table 2.

Comparative Example 1

Fluorescence signals derived from fluorescein were analyzed in the same manner as in Experimental Example 1 except that the compound 7 used in Experimental Example 1 was changed to fluorescein. As a result, it was found that fluorescein is lowly incorporated by a cell population as a whole and cannot identify hematopoietic stem cells.

Comparative Example 2

Fluorescence signals derived from Mito Tracker® Green FM were analyzed in the same manner as in Experimental Example 1 except that the compound 7 used in Experimental Example 1 was changed to Mito Tracker® Green FM. As a result, it was found that Mito Tracker® Green FM stains a cell population as a whole and hence cannot identify hematopoietic stem cells.

It was revealed based on the above-mentioned Experimental Examples 1 to 17 that hematopoietic stem cells can be identified and separated by using the hematopoietic stem cell identification probe of the present invention.

The identification of hematopoietic stem cells by using the respective dye compounds was as follows.

The identification was evaluated in the following three grades A to C:
A: Hematopoietic stem cells are identified very well.
B: Hematopoietic stem cells are identified well.
C: Hematopoietic stem cells are poorly identified.

TABLE 2

|  | Dye compound | Identification of hematopoietic stem cells |
|---|---|---|
| Experimental Example 1 | Compound 7 | A |
| Experimental Example 2 | Compound 8 | A |
| Experimental Example 3 | Compound 9 | A |
| Experimental Example 4 | Compound 10 | A |
| Experimental Example 5 | Compound 11 | A |
| Experimental Example 6 | Compound 12 | A |
| Experimental Example 7 | Compound 13 | A |
| Experimental Example 8 | Compound 14 | A |
| Experimental Example 9 | Compound 15 | A |
| Experimental Example 10 | Compound 16 | B |
| Experimental Example 11 | Compound 17 | A |
| Experimental Example 12 | Compound 18 | A |
| Experimental Example 13 | Compound 19 | B |
| Experimental Example 14 | Compound 20 | B |
| Experimental Example 15 | Compound 21 | A |
| Experimental Example 16 | Compound 22 | A |
| Experimental Example 17 | Compound 23 | A |
| Comparative Example 1 | Fluorescein | C (not stained at all) |
| Comparative Example 2 | MitoTracker Green FM | C (all stained) |

Experimental Example 18

Cells collected from a mouse were subjected to the exposure to the compound 7 and a blocking treatment in the same manner as in Experimental Example 1. In order to evaluate incorporation of antibody markers, used as test substances, of an anti CD48 antibody and an anti CD150 antibody by hematopoietic stem cells, the blocked cells were further stained with the anti CD48 antibody and the anti CD150 antibody. Furthermore, the resulting cells were subjected to dead cell staining with TO-PRO-3. Next, the cells were analyzed with an FACS Canto II flow cytometer manufactured by BD Biosciences. In the analysis, cell populations having a low TO-PRO-3 signal were regarded as a target, so that the analysis could be performed on a cell population excluding dead cells.

Figure 3:
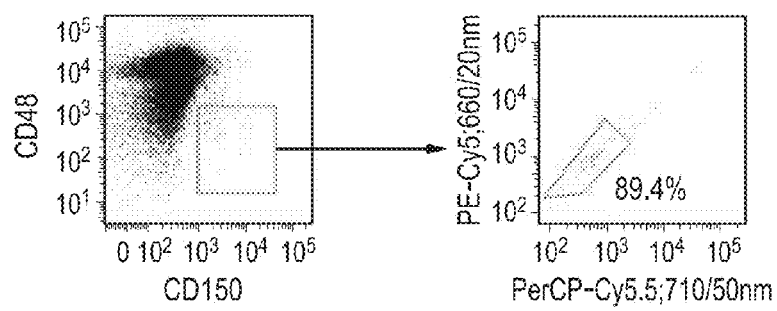
FIG. 3 is a diagram of a cytogram of bone marrow cells of Experimental Example 18 developed based on a fluorescent antibody markers and a cytogram of a hematopoietic stem cell fraction obtained by using the fluorescent antibody markers developed with respect to the two kinds of the fluorescent signals derived from the compound 7.

As a result, it was found, as illustrated in FIG. 3, that 89.4% of cells of a CD48 negative and CD150 positive fraction were present in a region, on a cytogram developed with respect to the two fluorescence signals derived from the compound 7 as in Experimental Example 1, where hematopoietic stem cells were identified.

It was revealed, based on this experimental example, that the effect of a test substance (an antibody marker) on hematopoietic stem cells can be evaluated/analyzed/screened by using the hematopoietic stem cell identification probe of the present invention.

Experimental Example 19

Cells collected from a mouse in the same manner as in Experimental Example 1 were exposed to the compound 7 in the presence of test substances of fumitremorgin C and digoxin (both in 1 µM). After performing a blocking treatment in the same manner as in Experimental Example 1, the resulting cells were stained with an anti c-Kit antibody, that is, a marker for hematopoietic stem cells and hematopoietic precursor cells. The cells were further subjected to the dead cell staining with TO-PRO-3. Next, the cells were analyzed with FACS Aria II cell sorter manufactured by BD Biosciences. In the analysis, cell populations having a low TO-PRO-3 signal were regarded as a target, so that the analysis could be performed on a cell population excluding dead cells.

Figure 4:
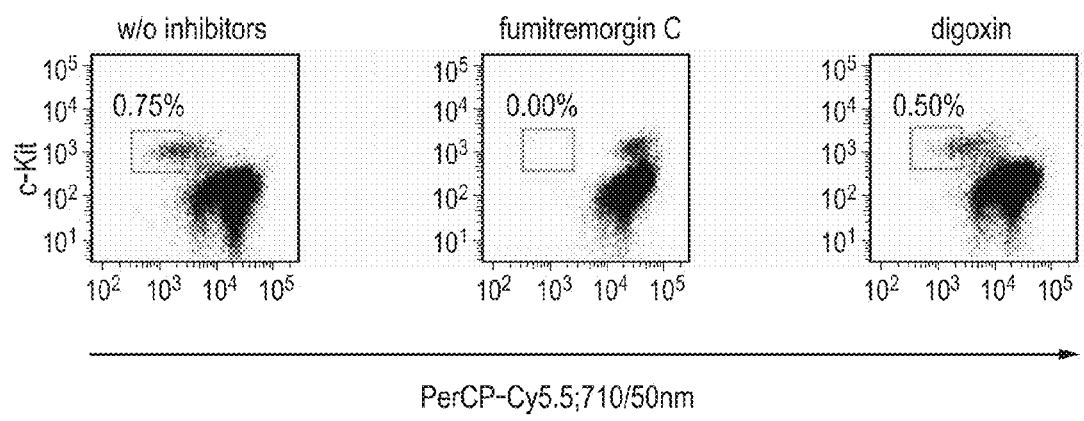
FIG. 4 is a diagram of cytograms of bone marrow cells exposed to the compound 7, cells simultaneously exposed to fumitremorgin C and cells exposed to digoxin in Experimental Example 19.

As a result, it was found, as illustrated in FIG. 4, that hematopoietic stem cells identified to be c-Kit positive, that is one of markers for hematopoietic stem cells and hematopoietic precursor cells, and to be negative for a compound 7-derived signal occupied 0.75% in the whole cells in the absence of an inhibitor (w/o inhibitors) but occupied 0.00% when the cells were exposed to fumitremorgin C and 0.50% when exposed to digoxin. In other words, hematopoietic stem cell groups that were c-Kit positive and negative for the compound 7-derived signal were confirmed to be reduced by adding the test substances.

It was revealed, based on this experimental example, that the effect of a test substance (a bioactive substance) on hematopoietic stem cells can be evaluated/analyzed/screened by using the hematopoietic stem cell identification probe of the present invention.

The hematopoietic stem cell identification probe provided by the present invention is a useful material with which hematopoietic stem cells can be simply, highly safely and inexpensively collected. Furthermore, with respect to screening and the like of a bioactive substance affecting hematopoietic stem cells, the hematopoietic stem cell identification probe of the present invention can be used for performing highly accurate screening with high throughput at low cost, and thus, the present invention provides a fundamental technology remarkably developing studies using hematopoietic stem cells and extremely effective in the industry and practical application.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-155812, filed Jul. 11, 2012, which is hereby incorporated by reference herein in its entirety.

What is claimed is:

1. A collection method for hematopoietic stem cells, the method comprising:
   contacting a hematopoietic stem cell identification probe with a cell population; and
   removing hematopoietic stem cells from the cell population based on incorporation of the hematopoietic stem cell identification probe into cells in the cell population, thereby collecting hematopoietic stem cells from the cell population,
wherein the hematopoietic stem cell identification probe comprises at least one compound represented by general formula (1):
   wherein the hematopoietic stem cell identification probe comprises at least one compound represented by general formula (1):

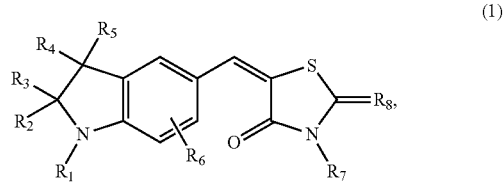

(1)

wherein $R_1$ represents a hydrogen atom, an alkyl group, an aralkyl group, an alkenyl group, an aryl group or a hetero ring group; each of R$_2$ to R$_5$ independently represents a hydrogen atom or an alkyl group, with R$_2$ and R$_4$ optionally bound to each other for forming a ring; R$_6$ represents a hydrogen atom, an alkyl group, an alkoxy group, or a halogen atom; R$_7$ represents an alkyl group or a carboxyalkyl group in which —CH$_2$—CH$_2$— of a carbon chain of the carboxy alkyl group is optionally substituted with —CONH—; and R$_8$ represents a sulfur atom or a group represented by general formula (4):

(4)

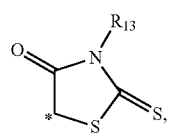

wherein * represents a binding site to the general formula (1) and R$_{13}$ represents an alkyl group, an aralkyl group, an allyl group, or a carboxyalkyl group.

2. The method according to claim 1, wherein R$_2$ and R$_4$ are bound to each other as a part of a cyclopentane ring in the general formula (1).

3. The method according to claim 1, wherein the at least one compound represented by the general formula (1) is a compound represented by general formula (2):

(2)

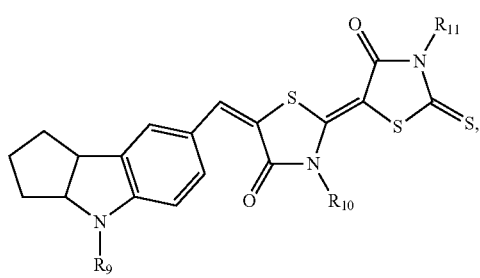

wherein R$_9$ represents an aryl group; R$_{10}$ represents an alkyl group or a carboxyalkyl group, wherein a carbon chain of the carboxyalkyl group has more than one carbon atom in which —CH$_2$—CH$_2$— of the carbon chain is substituted with —CONN—; and R$_{11}$ represents an alkyl group, an aralkyl group, an allyl group, or a carboxyalkyl group.

4. The method according to claim 1, wherein the at least one compound represented by the general formula (1) is a compound represented by general formula (3):

(3)

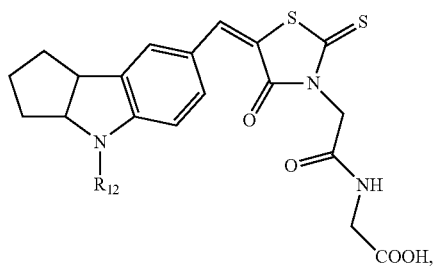

wherein R$_{12}$ represents an aryl group.

5. The method according to claim 1, wherein the at least one compound represented by the general formula (1) is at least one selected from the group consisting of compounds represented by formulae (7), (18), (19), (22), and (23):

(7)

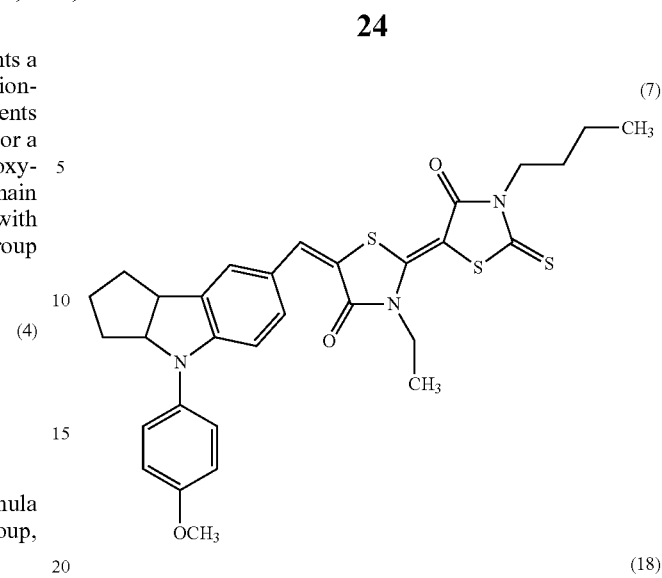

(18)

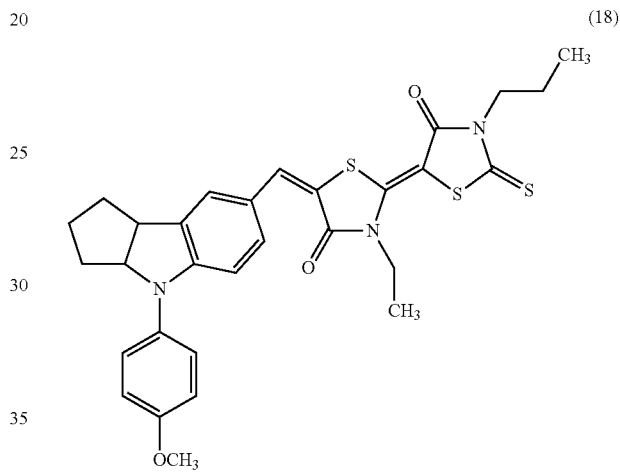

(19)

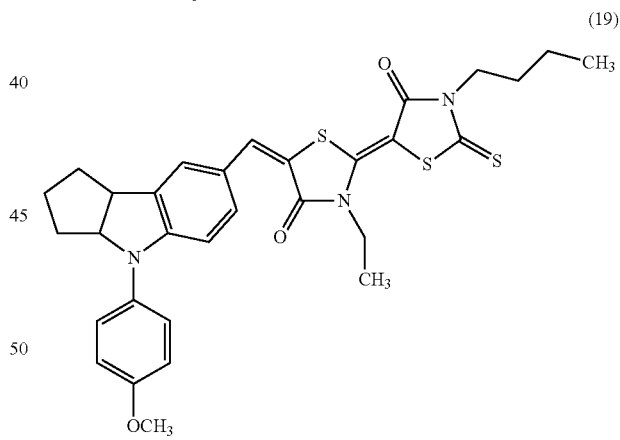

(22)

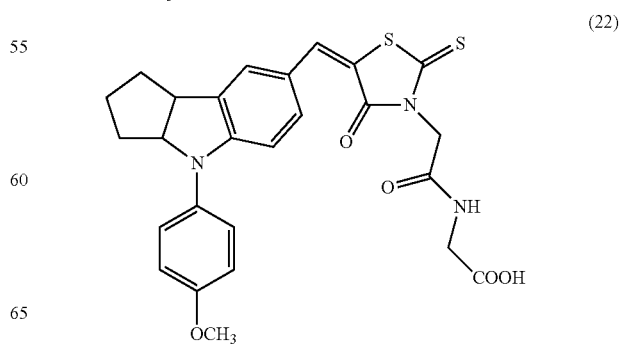

-continued

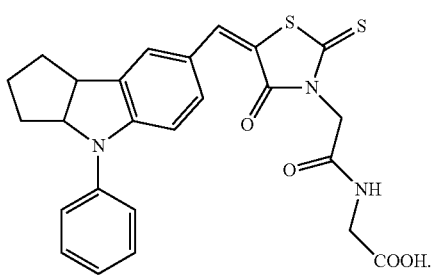
(23)

6. An identification method for hematopoietic stem cells in cell population, the method comprising:

contacting a hematopoietic stem cell identification probe with a cell population;

identifying hematopoietic stem cells contained in the cell population based on incorporation of the hematopoietic stem cell identification probe into cells in the cell population wherein the hematopoietic stem cell identification probe comprises at least one compound represented by general formula (1):

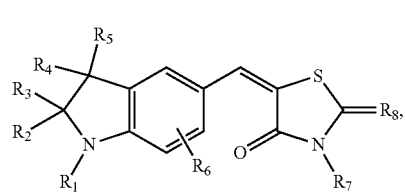
(1)

wherein $R_1$ represents a hydrogen atom, an alkyl group, an aralkyl group, an alkenyl group, an aryl group or a hetero ring group; each of $R_2$ to $R_5$ independently represents a hydrogen atom or an alkyl group, with $R_2$ and $R_4$ optionally bound to each other for forming a ring; $R_6$ represents a hydrogen atom, an alkyl group, an alkoxy group, or a halogen atom; $R_7$ represents an alkyl group or a carboxyalkyl group, wherein a carbon chain of the carboxyalkyl group has more than one carbon atom in which —$CH_2$—$CH_2$— of the carbon chain is substituted with —CONH—; and $R_8$ represents a sulfur atom or a group represented by general formula (4):

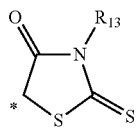
(4)

wherein * represents a binding site to the general formula (1) and $R_{13}$ represents an alkyl group, an aralkyl group, an allyl group, or a carboxyalkyl group.

7. The method according to claim 6, wherein $R_2$ and $R_4$ are bound to each other as a part of a cyclopentane ring in the general formula (1).

8. The method according to claim 6, wherein the at least one compound represented by the general formula (1) is a compound represented by general formula (2):

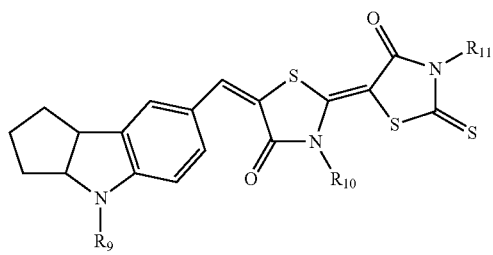
(2)

wherein $R_9$ represents an aryl group; $R_{10}$ represents an alkyl group or a carboxyalkyl group, wherein a carbon chain of the carboxyalkyl group has more than one carbon atom in which —$CH_2$—$CH_2$— of the carbon chain is substituted with —CONN—; and $R_{11}$ represents an alkyl group, an aralkyl group, an allyl group, or a carboxyalkyl group.

9. The method according to claim 6, wherein the at least one compound represented by the general formula (1) is a compound represented by general formula (3):

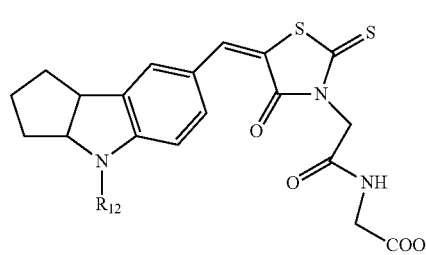
(3)

wherein $R_{12}$ represents an aryl group.

10. The method according to claim 6, wherein the at least one compound represented by the general formula (1) is at least one selected from the group consisting of compounds represented by formulae (7), (18), (19), (22), and (23):

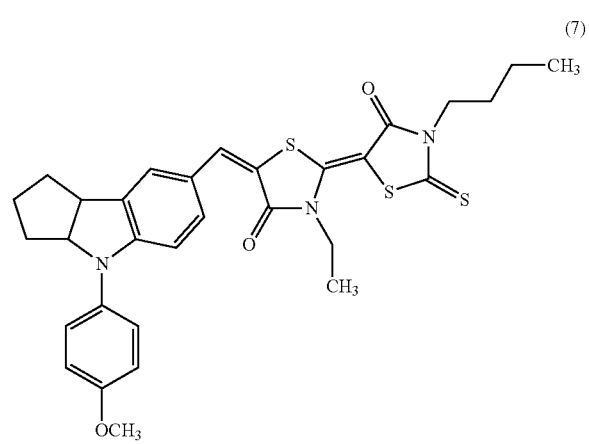
(7)

-continued

(18)
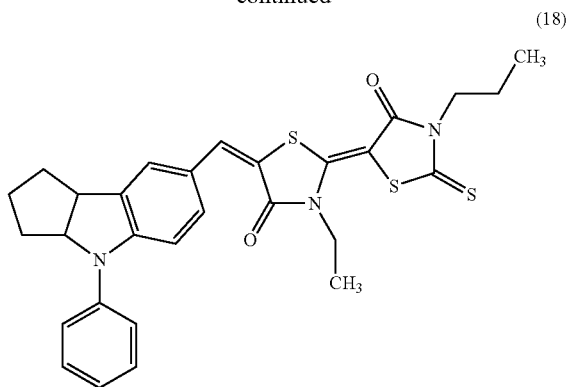

(19)
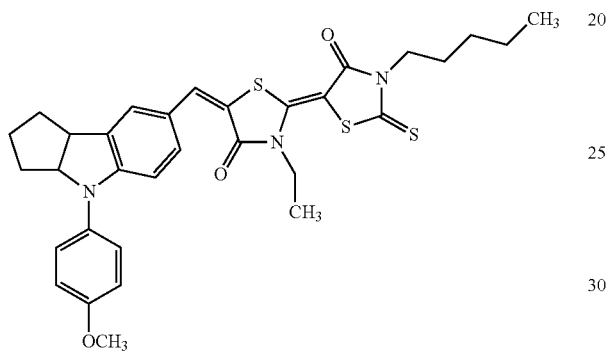

(22)
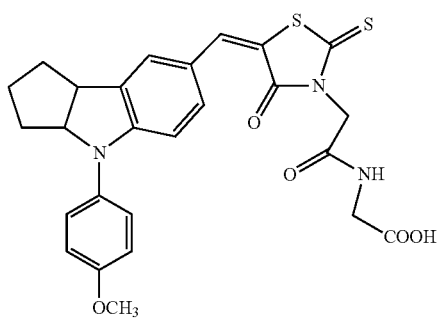

(23)
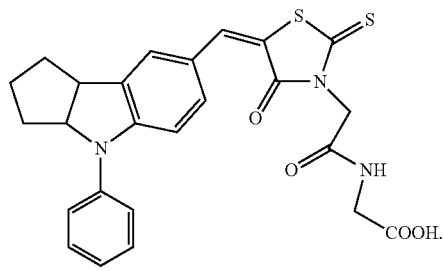

11. An identification method for hematopoietic stem cells in cell population, the method comprising:
  contacting a hematopoietic stem cell identification probe with a cell population;
  identifying hematopoietic stem cells contained in the cell population based on incorporation of the hematopoietic stem cell identification probe into cells in the cell population wherein the hematopoietic stem cell identification probe comprises at least one compound represented by general formula (1):

(1)
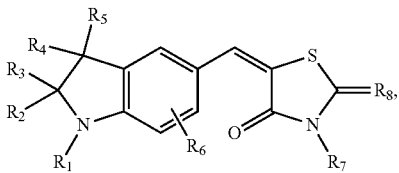

wherein $R_1$ represents a hydrogen atom, an alkyl group, an aralkyl group, an alkenyl group, an aryl group or a hetero ring group; each of $R_2$ to $R_5$ independently represents a hydrogen atom or an alkyl group, with $R_2$ and $R_4$ optionally bound to each other for forming a ring; $R_6$ represents a hydrogen atom, an alkyl group, an alkoxy group, or a halogen atom; $R_7$ represents an alkyl group or a carboxyalkyl group, wherein a carbon chain of the carboxyalkyl group has more than one carbon atom in which —$CH_2$—$CH_2$— of the carbon chain is substituted with —CONH—; and $R_8$ represents a sulfur atom or a group represented by general formula (4):

(4)
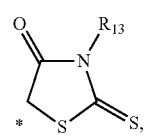

wherein * represents a binding site to the general formula (1) and $R_{13}$ represents an alkyl group, an aralkyl group, an allyl group, or a carboxyalkyl group, and wherein the at least one compound represented by the general formula (1) emits fluorescence when excited with light of a wavelength of 400 nm to 700 nm.

12. The method according to claim 11, wherein a cell having low incorporation of the hematopoietic stem cell identification probe is identified as a hematopoietic stem cell.

13. The method according to claim 11, wherein $R_2$ and $R_4$ are bound to each other as a part of a cyclopentane ring in the general formula (1).

14. The method according to claim 11, wherein the at least one compound represented by the general formula (1) is a compound represented by general formula (2):

(2)
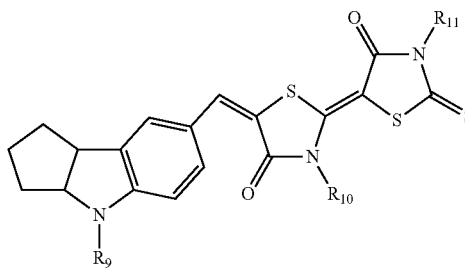

wherein $R_9$ represents an aryl group; $R_{10}$ represents an alkyl group or a carboxyalkyl group, wherein a carbon chain of the carboxyalkyl group has more than one carbon atom in which —$CH_2$—$CH_2$— of the carbon chain is substituted with —CONN—; and $R_{11}$ represents an alkyl group, an aralkyl group, an allyl group, or a carboxyalkyl group.

15. The method according to claim 11, wherein the at least one compound represented by the general formula (1) is a compound represented by general formula (3):

(3)

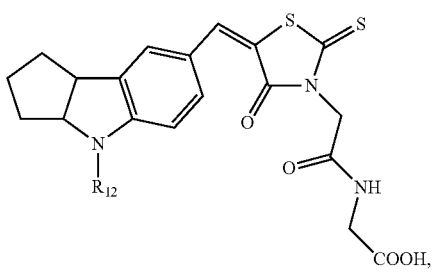

wherein $R_{12}$ represents an aryl group.

16. The method according to claim 11, wherein the at least one compound represented by the general formula (1) is at least one selected from the group consisting of compounds represented by formulae (7), (18), (19), (22), and (23):

(7)

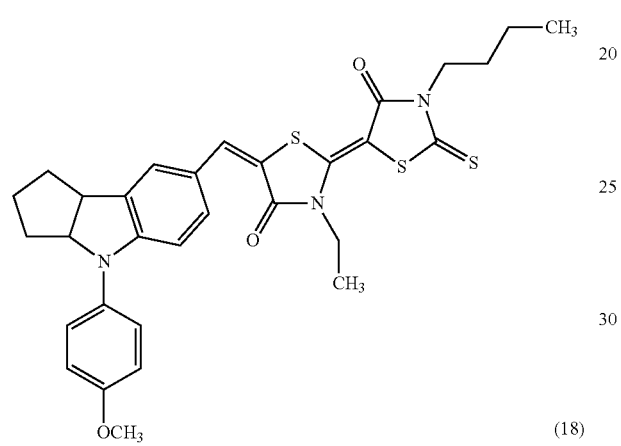

(18)

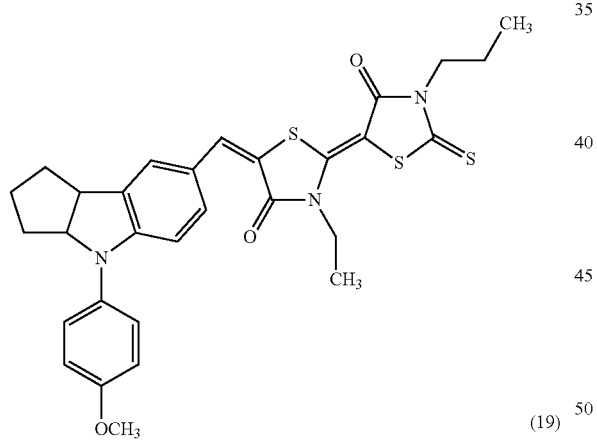

(19)

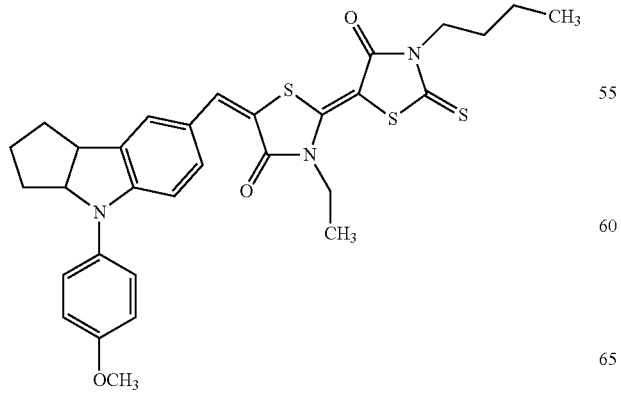

-continued (22)

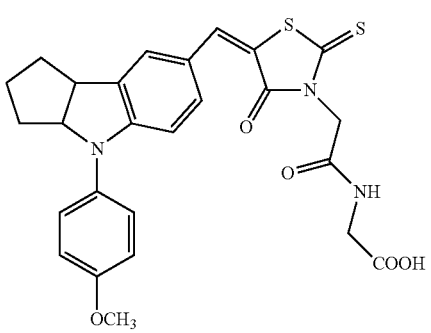

(23)

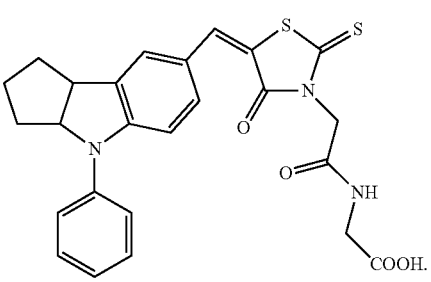

17. A method for evaluating a cell population, the method comprising:

contacting a hematopoietic stem cell identification probe with a cell population;

detecting incorporation of the hematopoietic stem cell probe into cells in the cell population, and obtaining information on the cell population based on the incorporation, wherein the hematopoietic stem cell identification probe comprises at least one compound represented by general formula (1):

(1)

wherein $R_1$ represents a hydrogen atom, an alkyl group, an aralkyl group, an alkenyl group, an aryl group or a hetero ring group; each of $R_2$ to $R_5$ independently represents a hydrogen atom or an alkyl group, with $R_2$ and $R_4$ optionally bound to each other for forming a ring; $R_6$ represents a hydrogen atom, an alkyl group, an alkoxy group, or a halogen atom; $R_7$ represents an alkyl group or a carboxyalkyl group, wherein a carbon chain of the carboxyalkyl group has more than one carbon atom in which —$CH_2$—$CH_2$— of the carbon chain is substituted with —CONH—; and $R_8$ represents a sulfur atom or a group represented by general formula (4):

(4)

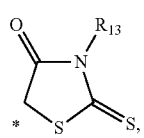

wherein * represents a binding site to the general formula (1) and $R_{13}$ represents an alkyl group, an aralkyl group, an allyl group, or a carboxyalkyl group.

18. The method according to claim 17, wherein $R_2$ and $R_4$ are bound to each other as a part of a cyclopentane ring in the general formula (1).

19. The method according to claim 17, wherein the at least one compound represented by the general formula (1) is a compound represented by general formula (2):

(2)

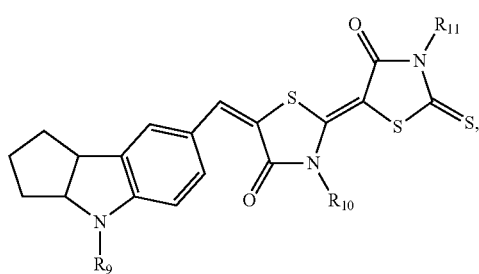

wherein $R_9$ represents an aryl group; $R_{10}$ represents an alkyl group or a carboxyalkyl group, wherein a carbon chain of the carboxyalkyl group has more than one carbon atom in which —$CH_2$—$CH_2$— of the carbon chain is substituted with —CONN—; and $R_{11}$ represents an alkyl group, an aralkyl group, an allyl group, or a carboxyalkyl group.

20. The method according to claim 17, wherein the at least one compound represented by the general formula (1) is a compound represented by general formula (3):

(3)

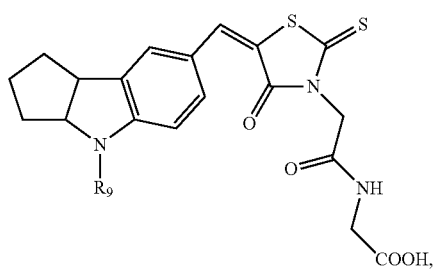

wherein $R_{12}$ represents an aryl group.

21. The method according to claim 17, wherein the at least one compound represented by the general formula (1) is at least one selected from the group consisting of compounds represented by formulae (7), (18), (19), (22), and (23):

(7)

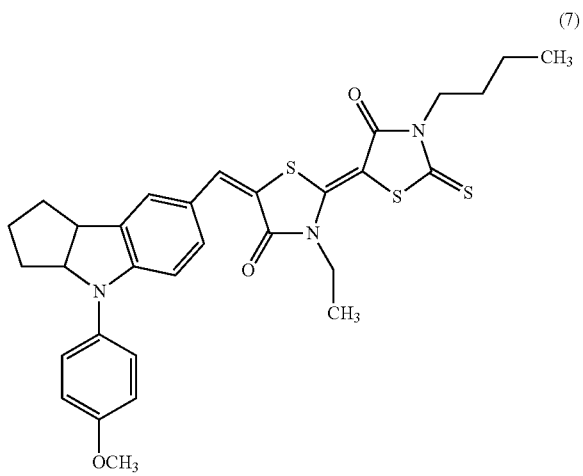

(18)

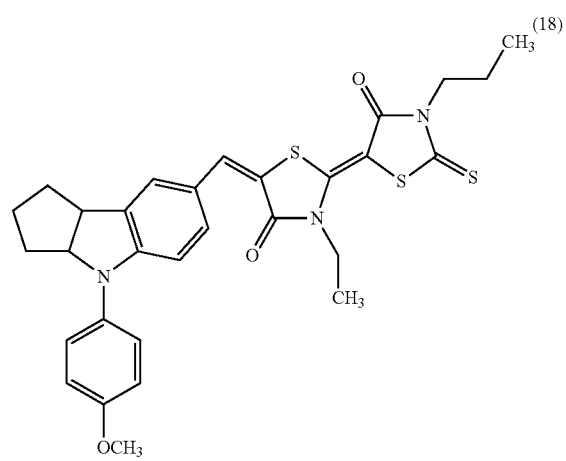

(19)

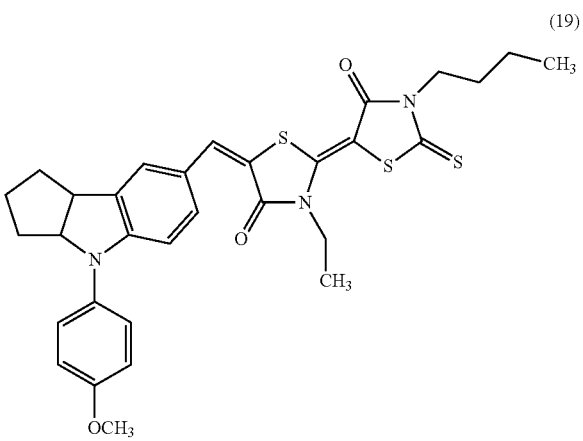

(22)

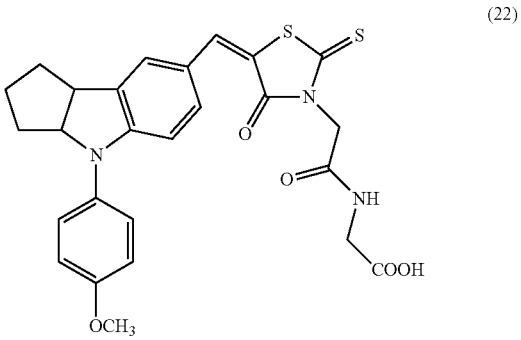

-continued
(23)
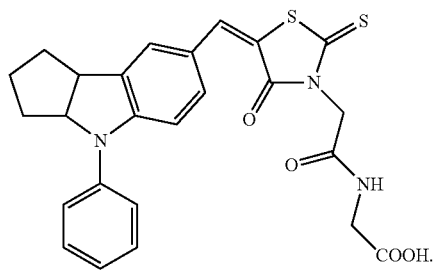
22. The method of claim 6, 11, 1 or 17, wherein $R^7$ is a carboxyl alkyl group which is selected from the group consisting of:
(1)
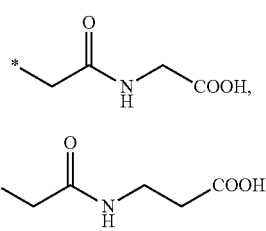
(2)
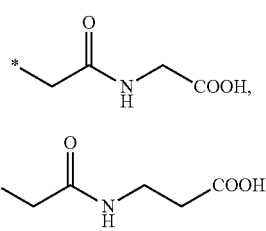
-continued
(3)
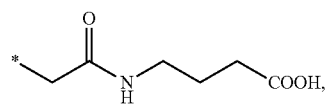
(4)
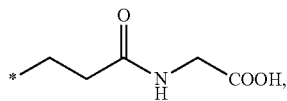
(5)
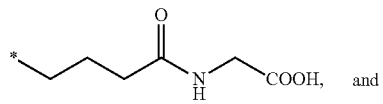 and
(6)
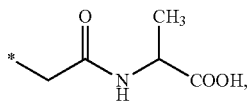
wherein * represents a binding site to the ring nitrogen.
* * * * *